(12) United States Patent
Csaba et al.

(10) Patent No.: US 6,686,481 B2
(45) Date of Patent: Feb. 3, 2004

(54) HIGHLY PURIFIED SIMVASTATIN COMPOSITIONS

(75) Inventors: Szabo Csaba, Debrecen (HU); Ferenc Korodi, Debrecen (HU); Melczer Istvan, Debrecen (HU); Szabolcs Salyi, Debrecen (HU); David Leonov, Rehovot (IL)

(73) Assignee: Plus Chemicals, B.V., Mijdrecht (NL)

( * ) Notice: Subject to any disclaimer, the term of this patent is extended or adjusted under 35 U.S.C. 154(b) by 0 days.

(21) Appl. No.: 09/916,662

(22) Filed: Jul. 26, 2001

(65) Prior Publication Data

US 2002/0115712 A1 Aug. 22, 2002

Related U.S. Application Data

(60) Provisional application No. 60/221,112, filed on Jul. 27, 2000.

(51) Int. Cl.[7] .............................................. C07D 315/00
(52) U.S. Cl. ..................................... 549/417; 549/420
(58) Field of Search ................................. 549/417, 420; 514/460

(56) References Cited

U.S. PATENT DOCUMENTS

| | | | |
|---|---|---|---|
| 4,293,496 A | 10/1981 | Willard | 549/292 |
| 4,444,784 A | 4/1984 | Hoffman et al. | 424/279 |
| 4,582,915 A | 4/1986 | Sleteinger et al. | 549/292 |
| 5,159,104 A | 10/1992 | Dabora et al. | 560/119 |
| 5,223,415 A | 6/1993 | Conder et al. | 435/125 |
| 6,100,407 A | 8/2000 | Van Dalen et al. | 549/196 |
| 6,252,091 B1 | 6/2001 | Zupancic et al. | 549/292 |

FOREIGN PATENT DOCUMENTS

| | | |
|---|---|---|
| EP | 0 299 656 B1 | 12/1990 |
| WO | WO95/13283 | 5/1995 |

OTHER PUBLICATIONS

A. Houck et al, "Liquid chromatographic determination of the known low level impurities in lovastatin bulk drug: An application of high–low chromatography", *Talanta*, vol. 40, No. 4, pp 491–494, 1993.

D. Askin; T.R. Verhoeven; T. M.–H. Liu and I. Shinkai, "Synthesis of Synvinolin: Extremely High Conversion Alkylation of an Ester Enolate", *The Journal of Organic Chemistry*, vol. 56, No. 16, pp 4929–4932, 1991.

*Primary Examiner*—Alan L. Rotman
*Assistant Examiner*—Raymond K Covington
(74) *Attorney, Agent, or Firm*—Kenyon & Kenyon

(57) ABSTRACT

The present invention relates to a process to prepare semi synthetic statins, to intermediates formed during said process and to highly purified simvastatin produced by the process.

17 Claims, No Drawings

HIGHLY PURIFIED SIMVASTATIN COMPOSITIONS

CROSS-REFERENCE TO RELATED APPLICATIONS

This application claims the benefit of U.S. provisional applications No. 60/221,112, filed Jul. 27, 2000, incorporated herein by reference.

FIELD OF THE INVENTION

The present invention relates to a process to prepare semi synthetic statins, to intermediates formed during said process and to highly purified simvastatin produced by the process.

BACKGROUND OF THE INVENTION

Statin drugs are currently the most therapeutically effective drugs available for reducing the level of LDL in the blood stream of a patient at risk for cardiovascular disease. This class of drugs includes lovastatin, simvastatin, pravastatin, compactin, fluvastatin and atorvastatin.

Simvastatin is the common medicinal name of the chemical compound butanoicacid, 2,2-dimethyl-,1,2,3,7,8,8a-hexahydro-3,7-dimethyl-8-[2-(tetrahydro-4-hydroxy-6-oxo-2H-pyran-2-yl)-ethyl]-1-naphthalenyl ester, [1S*-[1a,3a,7b,8b(2S*,4S),-8ab]]. (CAS Registry No. 79902-63-9.) The molecular structure of simvastatin is shown below with atoms labeled to indicate numbering of the atoms.

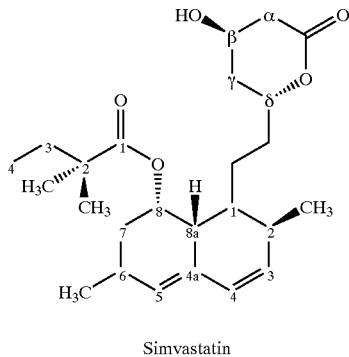

Simvastatin

Lovastatin is the common medical name of the chemical compound [1S-[1α(R*),3α,7β;8β(2S*,4S*),8aβ]]-1,2,3,7,8,8a-hexahydro-3,7-dimethyl-8-[2-(tetrahydro-4-hydroxy-6-oxo-2H-pyran-2-yl ethyl]-1-naphthalenyl 2-methylbutanoate. (CAS Registry No. 75330-75-5.) The molecular structure of lovastatin is shown below with atoms labeled to indicate numbering of the atoms.

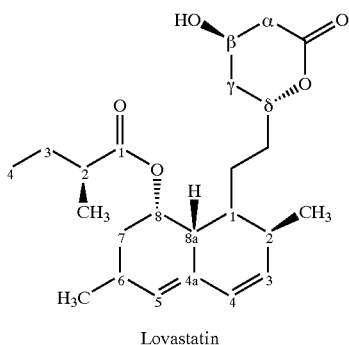

Lovastatin

Lovastatin possess a 2-methylbutyryl ester side chain at the 8-position of the hexahydronaphthalene ring system. In contrast, simvastatin possess a 2,2-dimethylbutyryl side chain at the 8-position of the hexahydronaphthalene ring system. It is known that simvastatin is a more effective agent than lovastatin for reducing the level of LDL in the blood stream.

The prior art discloses methods for converting lovastatin to simvastatin. U.S. Pat. No. 4,582,915, incorporated herein by reference, discloses converting mevinolin, compactin and dihydro- and tetrahydro derivatives thereof to more active HMG-CoA reductase inhibitors by C-methylation of the natural 2(S)-methylbutyryloxy side chain to form a 2,2-dimethylbutyryloxy side chain.

U.S. Pat. No. 5,223,415 incorporated herein by reference, discloses the enzymatic hydrolysis of lovastatin acid, by treating lovastatin acid with Clonostachys compactiuscula ATCC 38009 or ATCC 74178, or a cell-free extract derived therefrom. The product is an inhibitor of HMG-CoA reductase and thus useful as anti-hypercholesterolemic agents. The product also serve as an intermediate for preparation of other HMG-CoA reductase inhibitors.

U.S. Pat. No. 4,293,496 incorporated herein by reference, discloses removal of the 2-methylbutyryl side chain by base hydrolysis of the ester of lovastatin with an alkali metal hydroxide, preferably LiOH. The products are useful as intermediates in the synthesis of antihypercholesterolemia agents.

U.S. Pat. No. 4,444,784, incorporated herein by reference, discloses the introduction of a new side chain to hydrolyzed lovastatin.

U.S. Pat. No. 5,159,104, incorporated herein by reference, discloses the formation of simvastatin, by the sequential acylation of a diol lactone to form a bis acylated intermediate followed by selective deacylation and lactone ring closure to form simvastatin.

SUMMARY OF THE INVENTION

The present invention provides substantially pure simvastatin which comprises less than about 0.1 weight % simva-oxolactone.

The present invention also provides substantially pure simvastatin which comprises less than about 0.1 weight % anhydrosimvastatin.

The present invention also provides substantially pure simvastatin which comprises less than about 0.1 weight % simvastatin dimer.

The present invention also provides substantially pure simvastatin which comprises less than about 0.1 weight % dihydrosimvastatin.

The present invention also provides substantially pure simvastatin which comprises less than about 0.1 weight % at least one compound selected from the group consisting of simva-oxolactone, anhydrosimvastatin, simvastatin dimer and dihydrosimvastatin.

The present invention also provides a pharmaceutical composition comprising substantially pure simvastatin and less than about 0.1 weight % simva-oxolactone.

The present invention also provides a pharmaceutical composition comprising substantially pure simvastatin and less than about 0.1 weight % anhydrosimvastatin.

The present invention also provides a pharmaceutical composition comprising substantially pure simvastatin and less than about 0.1 weight % simvastatin dimer.

The present invention also provides a pharmaceutical composition comprising substantially pure simvastatin and less than about 0.1 weight % dihydrosimvastatin.

The present invention also provides a pharmaceutical composition comprising substantially pure simvastatin and less than about 0.1 weight % of at least one compound selected from the group consisting of simva-oxolactone, anhydrosimvastatin, simvastatin dimer and dihydrosimvastatin.

According to another aspect, the present invention relates to a process for the formation of highly purified simvastatin from lovastatin, comprising the steps of: lactone ring opening by reacting lovastatin with an amine to form an amid; protecting a 1,3-diol moiety with a protecting group; removing a 2-methylbutyryl group attached by an ester linkage through an oxygen at position 8 of a hexahydronaphthalene ring; attaching a 2,2-dimethylbutyrate group by forming an ester linkage to a hydroxyl at position 8; removal of a protecting group; conversion of the amid to an acid salt; and, lactone ring closing to form simvastatin.

According to another aspect, the present invention relates a process for the formation of a semisynthetic statin of Formula I,

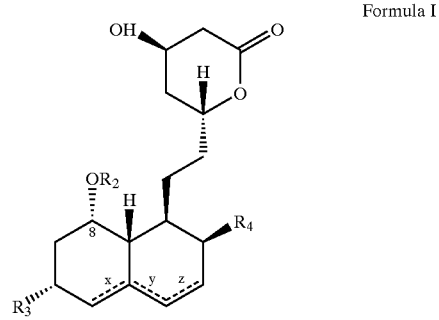

Formula I from a statin of Formula II,

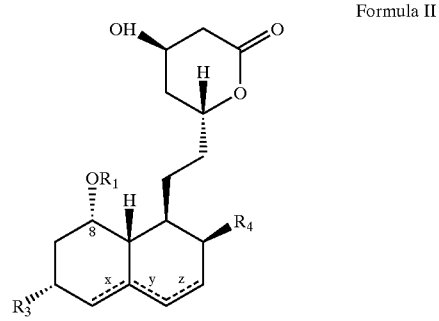

Formula II which comprises the steps of: lactone ring opening by reacting the statin of Formula II with an amine to form an amid; protecting a 1,3-diol moiety with a protecting group; removing a 2-methylbutyryl group attached by an ester linkage through an oxygen at position 8 of a hexahydronaphthalene ring; attaching a 2,2-dimethylbutyrate group by forming an ester linkage to a hydroxyl at position 8; removal of the protecting group; conversion of the amid to an acid salt; and, lactone ring closing to form the semisynthetic statin of Formula I wherein $R_1$ and $R_2$ are both acyl groups linked to the oxygen through an ester bond and $R_3$ and $R_4$ are independently selected from the group consisting of —H, —OH, —$C_{1-10}$ alkyl, —$C_{6-14}$ aryl, and —$C_{6-14}$ aryl-$C_{1-3}$.

DETAILED DESCRIPTION OF THE INVENTION

The present invention provides substantially pure simvastatin which comprises less than about 0.1 weight % simva-oxolactone.

The present invention also provides substantially pure simvastatin which comprises less than about 0.1 weight % anhydrosimvastatin.

The present invention also provides substantially pure simvastatin which comprises less than about 0.1 weight % simvastatin dimer.

The present invention also provides substantially pure simvastatin which comprises less than about 0.1 weight % dihydrosimvastatin.

The present invention also provides substantially pure simvastatin which comprises less than about 0.1 weight % at least one compound selected from the group consisting of simva-oxolactone, anhydrosimvastatin, simvastatin dimer and dihydrosimvastatin.

The present invention also provides a pharmaceutical composition comprising substantially pure simvastatin and less than about 0.1 weight % simva-oxolactone.

The present invention also provides a pharmaceutical composition comprising substantially pure simvastatin and less than about 0.1 weight % anhydrosimvastatin.

The present invention also provides a pharmaceutical composition comprising substantially pure simvastatin and less than about 0.1 weight % simvastatin dimer.

The present invention also provides a pharmaceutical composition comprising substantially pure simvastatin and less than about 0.1 weight % dihydrosimvastatin.

The present invention also provides a pharmaceutical composition comprising substantially pure simvastatin and less than about 0.1 weight % of at least one compound selected from the group consisting of simva-oxolactone, anhydrosimvastatin, simvastatin dimer and dihydrosimvastatin.

Method for Producing a Highly Purified Simvastatin

According to another aspect, the present invention relates to a process for the formation of highly purified simvastatin from lovastatin, comprising the steps of: lactone ring opening by reacting lovastatin with an amine to form an amid; protecting a 1,3-diol; removing a 2-methylbutyryl group attached by an ester linkage through an oxygen at position 8 of a hexahydronaphthalene ring; attaching a 2,2-dimethylbutyrate group by forming an ester linkage to a hydroxyl at position 8; removing the protecting; conversion of the amid to an acid salt; and, lactone ring closing to form simvastatin.

The conversion of lovastatin to simvastatin as provided by the invention is shown in Scheme I.

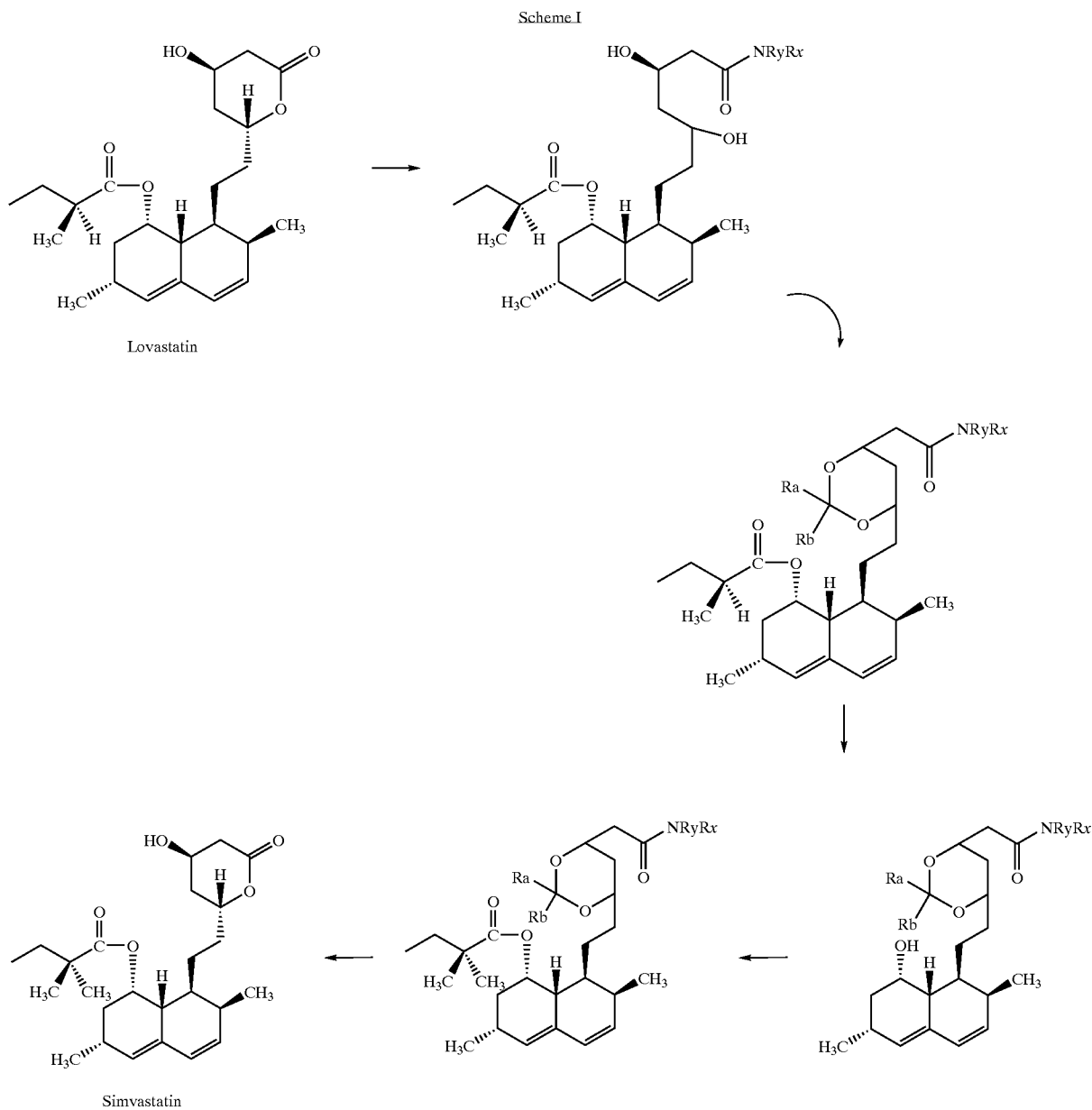

Scheme I

The lactone ring opening step is preferably performed by reacting the lactone with ammonia, a primary amine, or a secondary amine. Preferably, the lactone ring opening step is performed by reacting the lactone with an amine selected from the group consisting of n-butyl amine, cyclohexylamine, piperidine and pyrrolidine.

Potential impurities which can be formed during the synthesis of simvastatin are shown in Scheme II.

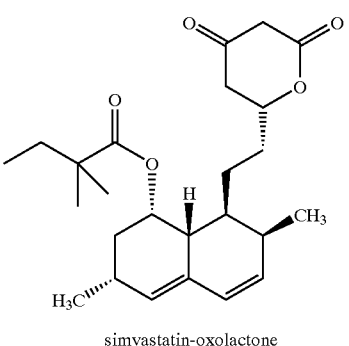

Scheme II simvastatin-oxolactone

-continued

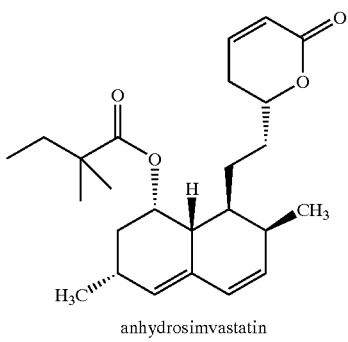

anhydrosimvastatin

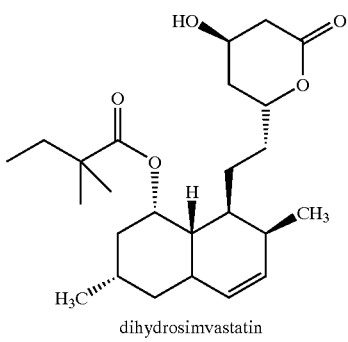

dihydrosimvastatin

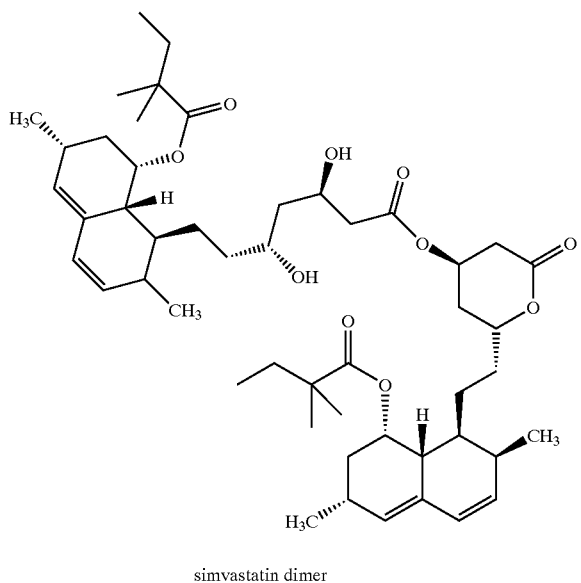

simvastatin dimer

Preferably, the substantially pure simvastatin synthesized by the method of the invention comprises less than about 0.1% weight simva-oxalactane.

Preferably, the substantially pure simvastatin by the method of the invention comprises less than about 0.1% weight anhydrosimvastatin.

Preferably, the substantially pure simvastatin synthesized by the method of the invention comprises less than about 0.1% weight dihydrosimvastatin.

The present invention also provides substantially pure simvastatin which comprises less than about 0.1% simvastatin dimer.

Optionally, the substantially pure simvastatin synthesized by the method of the invention may be synthesized from an of impure mixture of lovastatin comprising as much as about 30% impurities.

Method for Producing a Highly Purified Statin

According to another aspect, the present invention relates to a process for the formation of a semisynthetic statin of Formula I,

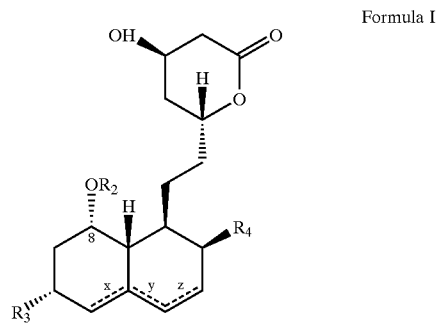

Formula I from a statin of Formula II,

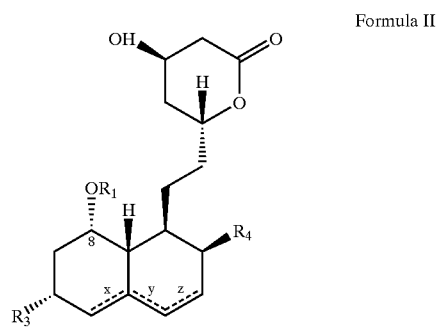

Formula II which comprises the steps of: lactone ring opening by reacting the statin of Formula II with an amine to form an amid; protecting a 1,3-diol; removing a $R_1$ group attached by an ester linkage through an oxygen at position 8 of a hexahydronaphthalene ring; attaching an $R_2$ group by forming an ester linkage to a hydroxyl at position 8; removing the protecting group; conversion of the amid to an acid salt; and, lactone ring closing to form the semi synthetic statin of Formula I, wherein $R_1$ and $R_2$ are both acyl groups linked to the oxygen through an ester bond and R3 and R4 are independently selected from the group consisting of —H, —OH, —$C_{1-10}$ alkyl, —$C_{6-14}$ aryl, and —$C_{6-14}$ aryl-$C_{1-3}$.

The conversion of the compound of Formula II to the compound of Formula I as provided by the invention is shown in Scheme III.

Scheme III

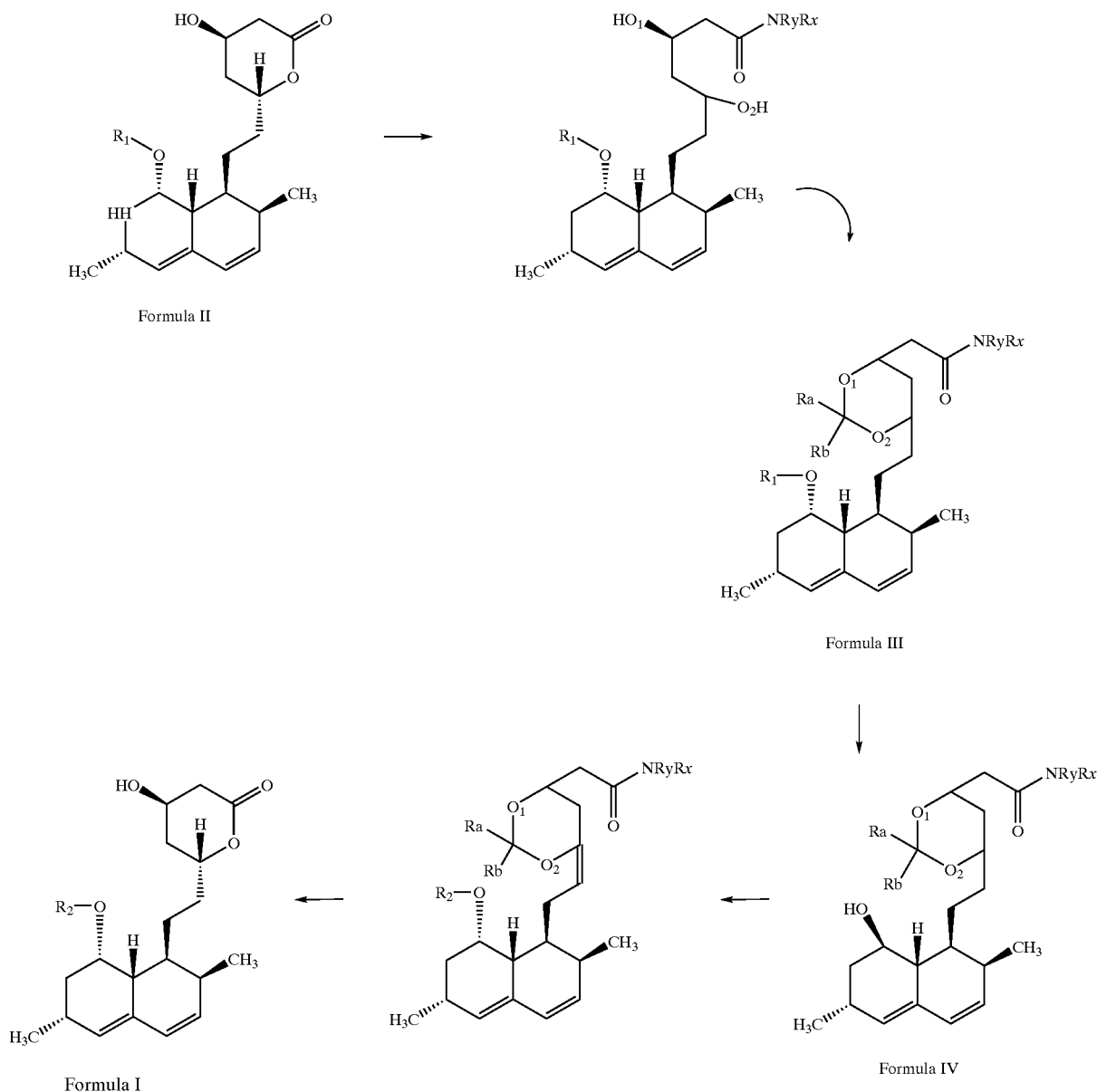

Formula II

Formula III

Formula IV

Formula I

Preferably, the semi synthetic statin of Formula I, synthesized by the method of the invention contains less than about 0.1% impurities.

Optionally, the semisynthetic statin of Formula I may be synthesized from an impure mixture a statin of Formula II comprising as much as about 30% impurities.

Preferably, $R_1$ is an acyl group of the form

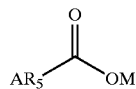

wherein OM is the oxygen which is the hexahydronaphthalene ring substituent at position 8, $R_5$ is selected from the group consisting of —$C_{1-15}$ alkyl, —$C_{3-15}$ cycloalkyl, —$C_{2-15}$ alkenyl, —$C_{2-15}$ alkynyl, -phenyl and -phenyl $C_{1-6}$ alkyl and A is a substituent of $R_5$ selected from the group consisting of hydrogen, a halogen, $C_{1-6}$ alkyl, $C_{1-6}$ alkoxy and $C_{6-14}$ aryl.

Preferably, $R_2$ is an acyl group of the form

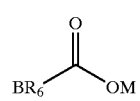

wherein OM is the oxygen which is the hexahydronaphthalene ring substituent at position 8, $R_6$ is selected from the group consisting of —$C_{1-15}$ alkyl, —$C_{3-15}$ cycloalkyl, —$C_{2-15}$ alkenyl, —$C_{2-15}$ alkynyl, -phenyl and -phenyl $C_{1-6}$ alkyl and B is a substituent of $R_6$ selected from the group consisting of hydrogen, a halogen, $C_{1-6}$ alkyl, $C_{1-6}$ alkoxy and $C_{6-14}$ aryl.

The dotted lines at X, Y and Z of Figure I and Figure II represent possible double bonds, the double bonds, when any are present, being either X and Z in combination or X, Y or Z alone.

Preferably, the lactone ring opening step is performed by reacting the lactone ring with ammonia, a primary amine, or a secondary amine. The lactone ring opening step may be performed by reacting the lactone with an amine selected from the group consisting of n-butylamine, cyclohexylamine, piperidine and pyrrolidine.

Preferably, the lactone ring opening is performed in an organic solvent. The organic solvent may be selected from toluene, cyclohexane, tetrahydrofurane, and acetonitrile.

Preferably, the lactone ring opening step is performed at a temperature above ambient temperature. Preferably the lactone ring opening step may be performed at a temperature of about 60° C.

Preferably, the lactone ring opening step includes removing unreacted amine after forming the amid. Methods for removing the unreacted amine include removing the amine by evaporation and/or washing an organic solution containing the amid with dilute acid.

The present invention also provides for a process for protecting 1,3-diol moiety with a protecting group. Methods for protecting hydroxyl groups are well known in the art and are disclosed for example in U.S. Pat. Nos. 6,100,407, 6,252,091, European Patent EP 299656, and WO 95/13283 incorporated herein by reference. The protecting group may be selected from the group which consists of an acetal, a ketal, a cyclic sulfate, a cyclic phosphate and a borate group.

In one embodiment of the present invention, the protecting group may be a ketal. The process of protecting the 1,3 diol may be performed by forming the ketal using a ketone. Ketal formation is optionally performed in an organic solvent. The organic solvent may be selected from the group which includes toluene, cyclohexane, tetrahydrofurane, acetonitrile, and ethyl acetate.

In an alternative embodiment, the protecting group may be an acetal. The process of protecting the 1,3 diol may be performed by foming the acetal using an aldehyde. Acetal formation is optionally performed in an organic solvent. The organic solvent may be selected from the group which includes toluene, cyclohexane, tetrahydrofurane, acetonitrile, and ethyl acetate.

In an alternative embodiment, the 1,3 diol may be protected by formation of a dioxane moiety to protect the 1,3-diol as shown in Scheme IV.

Scheme IV

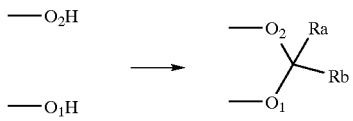

In an alternative embodiment, the 1,3-diol may be protected by formation of an acetal defined as

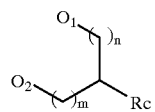

wherein $R_c$ may be selected from the groups comprising hydrogen, halogen, $C_{1-6}$ alkyl-, $C_{1-6}$ alkoxy, $C_{6-14}$ aryl as for instance phenyl or aromatic heterocycle and m, n, are each independently 0–10.

The present invention also provides for protective groups, such as for instance:

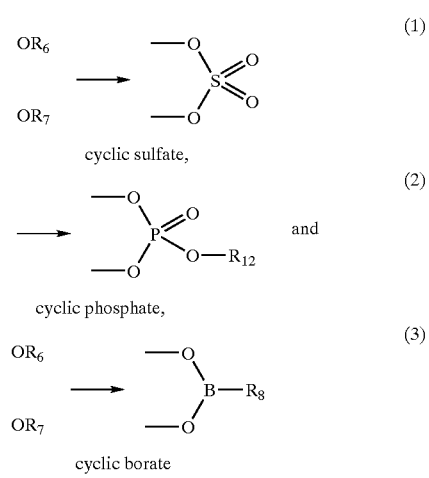

cyclic sulfate, (1)

cyclic phosphate, (2)

cyclic borate (3)

Preferably the protecting step is performed at a temperature from about 5° C. to about 50° C. Most preferably, the protecting step is performed at from about 20° C. to about 25° C.

Preferably, the protecting step is performed in the presence of a catalytic reagent. The catalytic reagent is preferably an acid. The acid may be selected from the group which consists of p-toluene sulfonic acid and sulfuric acid.

In one embodiment, the step of removing $R_1$ includes reducing the statin of Formula III with a reducing agent. The reducing agent may be selected from the group consisting of lithium aluminum hydride, aluminum hydride and diisobutylaluminum hydride. The reduction step is preferably performed in an inert solvent. The inert solvent may be selected from the group consisting of toluene and tetrahydrofuran. The reduction step may further include neutralizing the remaining reducing agent with water.

The reduction step is preferably performed at a temperature of about 0° C. to about 30° C. The reduction step is preferably performed at a temperature of about 5° C. to about 10° C.

In one embodiment the process of removing $R_1$ may includes reacting the statin of Formula III with an organometallic reagent in an inert solvent.

The organometallic reagent may be a Grignard reagent. The temperature of reacting the statin of Formula III with the Grignard reagent is preferably performed from about –10° C. to about 20° C. Preferably, the temperature of reacting the statin of Formula III is from about –5° C. to about 10° C.

Alternatively, the organometallic reagent may be an alkyl lithium derivative. The alkyl lithium reagent is preferably n-butlylithium. The temperature of reacting the statin of Formula III with the alkyl lithium is preferably from about –70° C. to about –20° C.

In one embodiment of the invention, the step of removing $R_1$ includes reacting the statin of Formula III with an amine. Preferably, the amine may be ammonia or a primary amine. Preferably, the molar ratio of the amine to Formula III may be about 1:1. Alternatively, the molar ratio of the amine to Formula III may be greater than about 1:1.

The step of removing $R_1$ may be performed in the presence of water. The step of removing $R_1$ may also be performed in the presence of an organic solvent.

Preferably, the step of removing $R_1$ is performed at a temperature of from about 100° C. to about 250° C. More preferably, the step of removing $R_1$ is performed at a temperature from about 130° C. to about 200° C.

Preferably, the step of removing $R_1$ is performed at a pressure greater then atmospheric pressure.

In a preferred embodiment, the step of attachment of $R_2$ includes acylation of the oxygen which is a hexahydronaphthalene ring substituent at position 8. The acylation step may include reacting the statin of Formula IV with an acid chloride. Alternatively, the acylation step may include reacting the statin of Formula IV with a free acid in the presence of carbodiimide. The carbodiimide may be 1,3 dicyclohexylcarbodiimide. In a further alternative embodiment, acylation may include reacting the statin of Formula IV with a symmetric anhydride in the presence of an organic solvent and a catalyst. Preferably, the catalyst is 4-dimethylaminopyridine.

Preferably, the acylation is performed at a temperature from about 20° C. to about 110° C. More preferably, the acylation is performed at a temperature from about 80° C. to about 110° C.

When the process of the invention includes protecting hydroxyl groups —$O_1H$ and —$O_2H$, the process of the invention may further comprise removing the protecting groups after the step of the attachment of $R_2$. Preferably, removing the protecting groups includes hydrolysis in a mixture of water and organic solvent in the presence of a catalyst. Preferably, the organic solvent is tetrahydrofuran. The catalyst may be an acid catalyst. The acid catalyst is preferably selected from the group which includes hydrogen chloride, sulfuric acid, and p-toluene sulfonic acid.

The step of removing the protecting groups is preferably performed at a temperature of from about 20° C. to about 100° C. More preferably step of removing the protecting groups is performed at a temperature of from about 30° C. to about 70° C.

The step of conversion of the amid to the acid salt preferably includes hydrolysis. The hydrolysis may be performed in a solution which includes a base, water and an organic solvent. The base is preferably selected from the group which includes sodium hydroxide and potassium hydroxide. The organic solvent is preferably selected from the group which includes methanol, ethanol, toluene, and tetrahydrofuran.

Preferably, the step of conversion of the amid to the acid salt includes forming a salt with a pharmaceutically acceptable counterion. The salt with the pharmaceutically acceptable counterion is preferably an ammonium salt.

Preferably, the step of lactone ring closing includes lactone formation in an organic solvent. The organic solvent is preferably selected from the group which consists of toluene, ethyl acetate, and cyclohexane. The lactone ring closing is preferably performed at an elevated temperature. The elevated temperature is preferably from about 60° C. to about 110° C. Most preferably the elevated temperature is from about 80° C. to about 110° C.

An alternative embodiment includes isolating the statin of Formula I by crystallization.

A Pharmaceutical Composition Containing Simvastatin

According to another aspect, the present invention relates to a pharmaceutical composition comprising the highly purified simvastatin disclosed herein and at least one pharmaceutically acceptable excipient. Such pharmaceutical compositions may be administered to a mammalian patient in a dosage form.

The dosage forms may contain substantially pure simvastatin or, alternatively, may contain substantially pure simvastatin as part of a composition. Whether administered in pure form or in a composition, the substantially pure simvastatin may be in the form of a powder, granules, aggregates or any other solid form. The compositions of the present invention include compositions for tableting. Tableting compositions may have few or many components depending upon the tableting method used, the release rate desired and other factors. For example, compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Dosage forms may be adapted for administration to the patient by oral, buccal, parenteral, ophthalmic, rectal and transdermal routes. Oral dosage forms include tablets, pills, capsules, troches, sachets, suspensions, powders, lozenges, elixirs and the like. The highly purified form of simvastatin disclosed herein also may be administered as suppositories, ophthalmic ointments and suspensions, and parenteral suspensions, which are administered by other routes. The most preferred route of administration of the simvastatin of the present invention is oral.

Capsule dosages will contain the solid composition within a capsule which may be coated with gelatin. Tablets and powders may also be coated with an enteric coating. The enteric-coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The currently marketed form of simvastatin is available as a 5 mg, 10 mg, 20 mg, 40 mg, 80 mg tablet which includes the following inactive ingredients: magnesium stearate, starch, talc, titanium dioxide, and other ingredients. Butylated hydroxyanisole is added as a preservative.

Lovastatin is supplied as 10 mg, 20 mg, and 40 mg tablets for oral administration. In addition to the active ingredient lovastatin, each tablet contains the following inactive ingredients: cellulose, lactose, magnesium stearate, and starch. Butylated hydroxyanisole (BHA) is added as a preservative.

The function and advantage of these and other embodiments of the present invention will be more fully understood from the examples below. The following examples are intended to illustrate the benefits of the present invention, but do not exemplify the full scope of the invention.

EXAMPLES

Experimental

The HPLC-analyses were carried out according to A. Houck et al, *Talanta* Vol. 40 (4), 491–494 (1993): Liquid Chromatopraphic determination of the known low level impurities in lovastatin bulk drug: an application of high-low chromatography HPLC equipment:
  Alliance Waters pomp/injector
  M996 diode array Waters
  Millennium data system Waters
  column: Prodigy 5 C8 250×4.6 mm (phenomenex)
Conditions:
  injection volume: 10 μl
  gradient flow profile (lineair)
  A=acetonitrile
  B=0.1% $H_3PO_4$.

| TIME min | FLOW ml/min | % A | % B |
|---|---|---|---|
| 0 | 1.5 | 60 | 40 |
| 1 | 1.5 | 60 | 40 |
| 5 | 1.5 | 80 | 20 |
| 8 | 1.5 | 90 | 10 |
| 16 | 1.5 | 90 | 10 |
| 20 | 1.5 | 60 | 40 | column temperature 30° C.
Detection at 200 nm and 237 nm.
The samples were mixed in acetonitrile with a concentration of 1.5 mg/ml.

| Retention times: | |
|---|---|
| dihydro simvastatin | 8.10 min (200 nm) |
| simvastatin acid | 5.77 min (237 nm) |
| lovastatin | 6.34 |
| simvastatin | 7.11 |
| anhydro simvastatin | 8.90 |
| dimer simvastatin | 15.36 |

Example 1
Formation of Lovastatin Piperidinamide:
A mixture of 1 g (2.5 mmol) of lovastatin, 10 ml (0.1 mol) of piperidine, 100 mg (0.82 mmol) of N,N-dimethylaminopyridine and 30 ml of toluene was refluxed for 36 hours. The mixture was cooled to RT and washed with 2×30 ml of 2 N HCl and 2+20 ml of water. The organic layer was dried with sodium sulfate, filtered and evaporated. The residue was stirred with hexane and the resulting precipitate was filtered to give 0.87 g of lovastatin piperidinamide as a white solid.

Example 2
Reaction of Lovastatin Butylamide with Thionylchloride:
0.76 g (7.5 mmol) of triethylamine was added to a solution of 1.2 g (2.5 mmol) of lovastatin butylamide in 20 ml of toluene. 0.45 g (3.7 mmol) of thionylchloride was added dropwise. After 1 hour at room temperature the reaction mixture was washed with water, dried (sodium sulphate), filtered and evaporated to give a brown oil.

Example 3
Reaction of Lovastatin Butylamide with Phosphorylchloride:
0.76 g (7.5 mmol) of triethylamine was added to a solution of 1.2 g (2.5 mmol) of lovastatin butylamide in 20 mil toluene. Next 0.58 g (3.8 mmol) of phosphorylchloride was added dropwise. After 1 h at room temperature the reaction mixture was filtered, dried (sodium sulphate), filtered and evaporated to give a brown oil.

Example 4
A. Formation of the Acetonide of Lovastatin Butylamide
A mixture of 40 g (98 mmol) of lovastatin and 60 ml of n-butylamine was refluxed for 1 hour, evaporated and coevaporated twice with 100 ml of toluene. The resulting crude amide was dissolved in 500 ml of acetone and 3 g of p-TsOH was added. The clear solution was stirred at room temperature (RT) for two hours at which time a solid was formed. The mixture was cooled to −10° C. for three hours and the solid was collected and dried to afford 45 g (88%) of the amide/acetonide as a white solid. From the mother-liquor another 5 g was obtained by partially evaporation of the solvent.

B. Alkylation of Amide/Acetonide Intermediate Formed in Step A:
The amide/acetonide (19.5 g, 37.6 mmol) in 280 ml THF/cyclohexane (4/1) was cooled to −40° C. and 113 ml 1M lithiumpyrrolide (prepared from pyrrolidine and n-butyllithim at −15° C.) was added maintaining the temperature at <−30° C. The solution was stirred at −35° C. for two hours and 5 ml MeI was added in one portion. The solution was stirred at −30° C. for one hour and the temperature was allowed to rise to −10° C. 300 ml of 1N HCl was added and the resulting mixture was refluxed for one hour. Ethyl acetate (300 ml) was added and the organic layer was washed with 100 ml of 3N HCl and evaporated. 300 ml of methanol and 125 ml of 2N NaOH were added to the residue. The mixture was refluxed for 12 hours and most of the methanol was evaporated. 120 ml of water and 300 ml of ethyl acetate were added and the pH was adjusted to 5 with 3N HCl. To the organic layer were added 60 ml of methanol and 25 ml of $NH_4OH$/methanol (⅓). The resulting mixture was stirred for one hour at room temperature and then cooled to 10° C. The solid was collected and dried. The yield was 13.5 g (80%) of simvastatin ammonium salt.

Example 5
Process for the Preparation of Simvastatin from Lovastatin by Reduction of the $R_1$ Ester Moiety
A. Formation of the Acetonide of Lovastatin Butlamide:
A mixture of lovastatin (40.5 g, 100 mmol) and 75 ml of n-butylamine was heated at reflux for 2 hour. The excess of amine was evaporated and coevaporated with 100 ml of toluene. To the crude amide was added 400 ml of acetone and 5 g of p-TsOH. The mixture was stirred at RT for 2 hour and then cooled in ice/water for 2 hours. The resulting solid was collected by filtration and dried. From the mother-liquor a second batch was obtained. Total yield 49 g (94–95%).

B1. Reduction of the Intermediate Formed in Step A with Lithiumaluminiumhydride:
The compound as formed in step A (45 g, 87 mmol) was dissolved in 200 ml of THF and added dropwise to a suspension of 7 g (2.1 equivalents) of lithiumaluminiumhydride ($LiAlH_4$) in 100 ml of THF at 10–15° C. in ca. 20 minutes. The mixture was stirred for 30 minute. The reaction mixture was treated with a solution of 20% KOH (exothermic). The resulting salts were removed by filtration and washed with 200 ml of THF. The combined filtrates were evaporated to afforded 35.5 g of a syrup.

B2. Reduction of the Intermediate Formed in Step A with Methylmagnesiumchloride (Grignard):
A solution of 2 g (3.9 mmol) of the compound as formed in step A, in 20 ml of THF was cooled to 0° C. A solution of 12 ml of 3M methylmagnesiumchloride was added dropwise in 20 minutes. After 18 hours at RT the lovastatin n-buylamide acetonide was converted completely.

B3. Reduction of the Intermediate Formed in Step A with n-butyllithium:

A solution of the compound as formed in step A (91 g, 1.9 mmol) in 25 ml THF was cooled to −50° C. A solution of 2.5 M n-butyllithium (2.74 ml) was added dropwise over a period of 10 minutes. After 18 hours stirring at RT the alcohol intermediate was formed.

C. Acylation of the Intermediate Formed in Step B and Conversion to Ammonium Salt of Simvastatin:

3 g of 4-dimethylaminopyridine in 300 ml of pyridine was added to a solution of 25 g (57 mmol) of the intermediate formed in step B and the mixture was heated to 50–55° C., preferably 50° C. 2,2-Dimethylbutyric acid chloride (50-ml) was added in one portion and the resulting mixture was stirred for 40 hours (HPLC—analysis showed complete conversion). To the reaction mixture 400 of ml water and 400 ml of ethyl acetate (EtOAc) was added. The organic layer was subsequently washed twice with 10% $NaHCO_3$ (400 ml), with water (400 ml) and with a solution of 10% HCl (400 ml). The organic layer was evaporated and dissolved in 200 ml of THF, 200 ml water was added, followed by 10 g of p-TsOH. The mixture was refluxed for 2 hours. EtOAc (400 ml) was added, followed by 300 ml water. The organic layer was washed twice with 10% $NaHCO_3$ (400 ml) and evaporated. The residue was dissolved in 300 ml of MeOH and 170 ml of 2N NaOH was added. The resulting mixture was refluxed for 3 hours and cooled to RT. Most of the MeOH was evaporated and 120 ml of water was added. The pH was adjusted to pH=7 with 2N HCl and 300 ml of EtOAc was added. The pH was further adjusted to pH=4 and the layers were separated. To the organic layer was added 100 ml of EtOH, followed by 40 ml of $NH_4OH$/MeOH (⅓). The mixture was stirred at −10° C. for 2 hours and the solid collected and washed with EtOAc and EtOH (cold). Yield 16 g (62%), HPLC-analysis gave 98,9% of the ammonium salt of simvastatin.

D. Conversion of the Simvastatin Ammonium Salt to Simvastatin:

A suspension of 9 g of the ammonium salt of simvastatin as formed in step C was heated in 250 ml of toluene at 100° C. for 6 hours. The mixture refluxed for an additional 30 minutes, filtered and evaporated. To the residue 100 ml of cyclohexane was added and the solution was evaporated again. The crude simvastatin was recrystallized from ca. 150 ml of cyclohexane to afford simvastatin as a white solid. Yield 85%, HPLC—analysis gave 98,4% of simvastatin.

Example 6

Process for the Preparation of Simvastatin from Lovastatin by Reduction of the $R_1$ Ester Moiety.

A: Preparation of the Acetonide of Lovastatin Butyl Amide.

A mixture of 950 g of lovastatin (2.4 mol), 8 L of toluene and 500 ml of n-butylamine (5 mol) is heated up to 85° C. under nitrogen. The solution is kept at 85° C.–95° C. during 2 hours, and is subsequently cooled to room temperature. Then 5L of 4 N sulfuric acid is added and the mixture is stirred during 5 minutes. The lower layer is removed, and 1.5 L (12 mol) of 2,2-dimethoxy propane are added to the upper layer. The solution is stirred during 30 minutes at room temperature, and thereafter the mixture is concentrated to 5.4 kg by evaporation at 55–60° C. under vacuum.

B: Reduction of the Intermediate Formed in Step A with Lithium Aluminum Hydride 5.8 L (5.5 kg, corresponding to 2.4 mol of the intermediate obtained in step A) of the concentrate obtained in step A is mixed with 2 L of toluene. The mixture is cooled to 0° C. under a nitrogen atmosphere. 6 L of a 1 N solution of Lithium aluminum hydride in toluene (6 mol $LiAlH_4$) is added over a period of 75 minutes, during which the temperature is kept below 8° C. The resulting mixture is stirred for 3 hours at 5–10° C., then 5.3 L of water was added over a period of 100 minutes keeping the temperature below 10–15° C. Subsequently, 5 L of 4 N sulfuric acid is added to the suspension and the mixture is stirred during 15 minutes. Hereafter, the layers are allowed to settle. The milky lower layer is removed, and the upper layer is washed with 4.5 L of water and with 6 L of aqueous 1 N sodium hydroxide solution. 6 L of the upper layer a removed by evaporation at 50–60° C. under vacuum (150–300 mm Hg).

C: Acylation of the Intermediate Obtained in Step B With 2.2-dimethl Butyryl Chloride To the solution of the alcohol intermediate in toluene obtained in step B, containing 2.4 mol of intermediate, 250 ml of toluene containing 35 g (0.29 mol) of 4-(N,N-dimethyl amino) pyridine, 1.6 L of triethylmine (11.4 mol) and 1.5 kg (11 mol) of 2.2-dimethyl butyryl chloride are added. The resulting solution is heated to 105–110° C., and stirred at this temperature during 10 hours under nitrogen. Hereafter, the resulting suspension is cooled to room temperature, and 3 L of 4 N sulfuric acid is added. The mixture is stirred for 5 minutes, and then the layers are allowed to separate. Subsequently the lower layer is removed, and the upper layer is washed with 2 l of 4 N sulfuric acid.

D: Preparation of Simvastatin Ammonium Salt

The reaction mixture obtained in Step C (circa 11 L) is mixed with 4.5 L of 4 N sulfuric acid. The mixture is subsequently heated at 70–75° C. during 3 hours, while nitrogen is led through the mixture. Then the mixture is allowed to cool to room temperature, and the lower layer is removed. The upper layer is cooled to 5° C. and washed with 2.5 L of 2 N sodium hydroxide. After removal of the lower layer, 6 L of 2 N sulfuric acid is added and stirred during 3 hours at room temperature, and then at 45–55° C. during 3 hours. The suspension is cooled to 5–10° C., thereafter 2.75 L of 4 N sulfuric acid is added while the temperature is kept below 10° C. Then the lower layer is removed, and 1 L of a concentrated $NH_4OH$ solution is added. Subsequently, the mixture is concentrated at 50–60° C. under vacuum in order to remove toluene and water. 3 L of ethyl acetate is added to the residue, and the mixture is stirred at 50° C. during 30 minutes to obtain a homogeneous suspension. The suspension is cooled to room temperature and filtered under vacuum. The filter cake is subsequently washed with 1 L of ethyl acetate and subsequently it is suspended in 4 L of ethyl acetate, heated at 50° C. for 90 minutes, the warm suspension is filtered and the filter cake is washed in ethyl acetate, yielding 891 g of crystals of simvastatin ammonium salt.

E: Preparation of Simvastatin 570 g of the ammonium salt crystals as obtained in step D are suspended in 13 L of toluene. Subsequently 2 L of water is added, and the pH is adjusted to 3 by addition of 4 N sulfuric acid. The mixture is stirred during 30 minutes, thereafter the lower layer is removed. The upper layer is subsequently washed with 2 L of water, and concentrated by evaporation of 4 L of toluene at 50–60° C. under vacuum. The remaining solution is heated at 85–92° C. under nitrogen during 2.5 hours. Then, the solution is cooled to 15° C., 3 L of water is added and the pH is adjusted to pH 8–8.5 by addition of a solution of 1 N NaOH. The lower layer is removed and 3 L of water is added to the upper layer followed by adjustment of the pH to 6 by adding 6N sulfuric acid. The lower layer is removed, and the upper layer is concentrated to 1 L by evaporation at 50–60° C. under vacuum. Subsequently 350 ml of n-hexane is added over a period of 1 hours at 50–60° C. Subsequently the mixture is stirred at 50–60° C. during 30 minutes and then slowly cooled to 15° C. over a period of 2 hours. The crystals are filtered and washed with 350 ml of a mixture of n-hexane/toluene (5/1), yielding 440 g of simvastatin.

Example 7

Process for the Preparation of Simvastatin Ammonium Salt by Reduction of the $R_1$ Ester Moiety of Lovastatin.

A. Formation of Lovastatin Cyclohexanamide:

A mixture of 5 g (0.012 mol) of lovastatin, 6 ml (0.052 mol) of cyclohexylamine and 50 ml of toluene was refluxed for 6 hours. The reaction mixture was cooled to RT and 20 ml of ethyl acetate was added. The mixture was washed with 2N HCl (2×30 ml) and water (2×20 ml). The organic layer was dried with sodium sulfate, filtered and evaporated to a volume of 15 ml. 50 ml of hexane was added and the precipitate was filtered to give 5.5 g of lovastatin cyclohexanamide as a white powder.

B. Formation of Lovastatin Cyclohexanamide Acetonide:

To a solution of 5 g (10 mmol) of lovastatin cyclohexanamide in 25 ml of acetone was added 300 mg (1.6 mmol) of p-TsOH. After 18 hours stirring at RT the solution was poured into a mixture of 50 ml ethyl acetate and 50 ml, 10% sodium bicarbonate solution. The ethyl acetate layer was separated, washed with 30 ml, 10% sodium bicarbonate solution, dried with sodium sulfate, filtered and evaporated. The residue was dissolved in toluene and which was subsequently evaporated to give 4.9 g of the acetonide of lovastatin cyclohexanamide.

C. Formation of Simvastatin Ammonium Salt:

A suspension of 836 mg (22 mmol) of lithiumaluminiumhydride in 15 ml of THF was cooled to 0° C. and a solution of 4.93 g (9.1 mmol) of the compound formed in step B, in 20 mol of THF was added dropwise over a period of 15 minutes. After 18 hours at RT the reaction mixture was cooled at 0° C. and 1 ml of water and of a 10% potassium hydroxide solution were added subsequently. The mixture was filtered over Celite and the THF was evaporated to give the corresponding 4.3 g (9 mmol) of alcohol intermediate.

D. Formation of Simvastatin Ammonium Salt:

A mixture of 4.3 g (9 mmol) of the alcohol intermediate, 40 ml of pyridine, 200 mg N,N-dimethylaminopyridine and 7.2 g (54 mmol) of 2,2-dimethylburyric acid chloride was stirred for 72 hours at 65° C. The mixture was cooled, 100 ml of toluene was added and the mixture was washed with 2×50 ml of a 10% sodium bicarbonate solution and 30 ml of brine. The toluene layer was dried with sodium sulfate, filtered and evaporated. The residue was dissolved in 100 ml of toluene, which was subsequently evaporated. The residue was dissolved in 20 ml of THF and 20 ml of water. Next, 2 g of p-TsOH was added and the solution was refluxed for 5 hours. The solution was poured into a mixture of 70 ml of toluene and 50 ml of 10% sodium bicarbonate solution. The organic layer was separated and washed with 30 ml of 10% sodium bicarbonate solution. The organic layer was dried, filtered and evaporated to give 4,8 g residue. The residue was dissolved in 70 ml of methanol and 40 ml of 2M NaOH. The reaction mixture was refluxed for 72 hours. The methanol was evaporated and the water layer was cooled to 0° C. The water layer was acidified to pH=5 with a 2N HCl solution. Next, 75 ml of ethyl acetate was added and the organic layer was separated. To the ethyl acetate was added 5 ml 25% of ammonia solution. The precipitate was filtered to give 1.1 g of the ammonium salt of simvastatin, with an overall yield of 27% from the acetonide of lovastatin cyclohexanamide.

Example 8

Preparation of Diacylated Simvastatin Butylamide

A. Silylation of Lovastatin Butylamide t-Butyl dimethylsilyl lovastatinbutylamide was prepared by literature procedure (Askin D; Verhoeven, T. R.; Liu, T,M. -H.; Shinkai, I. Jorg.Chem, 1991, 56, 4929) and obtained with a yield of 68% (crude meterial), HPLC $R_f$=12.87.

B. Reduction of t-butyl Dimethylsilyl Lovastatin Butylamide

A solution of t-butyl dimethylsilyl lovastatin butylamide (1,65 g, 2.34 mmol) in THF (30 ml) was added to a 2M solution of $LiAlH_4$.2THF in toluene (6 ml, 2.5 eq,) at 0° C. The reaction mixture was stirred for 2 h, after which moist sodium sulfate ($Na_2SO_4.nH_2O$) was added until gas evolution ceased. Attempts to filter the slurry over a glass funnel (P2) with Celite layer failed. The reaction mixture was poured in dilute HCl (<1N). The water layer was extracted with diethyl ether. The organic layer was washed with brine, dried ($Na_2SO_4$) and evaporated. Yield: 1.07 g (89%) HPLC: $R_f$:9.27

C. Acylation of t-butyl Silyl Protected Lovastatin Butylamide Alcohol

To a solution of the alcohol intermediate obtained in step 8B (360 mg, 0.58 mmol) and triethylamine (0.32 ml) in toluene (10 ml), 2,2-dimethylbutyryl chloride was added. (0.31 g, 4 eq.). The reaction mixture was heated to reflux for 10 h (standard procedure). HPLC analysis showed a mixture of compounds among which the desire diacylated product ($R_f$=15,81). Removal of the protecting groups according to the method described in Askin D; Verhoevven, T. R.; Liu, T,M. -H.; Shinkai, I. *J. Org. Chem*, 1991, 56, 4929) and obtained with a yield of 68% (crude material), HPLC $R_f$:12.87.

Example 9

Preparation of the Diacetylbenzylidene Derivative of Lovastatin:

A) Formation of the Benzylidene Derivative of Lovastatin Butylamide

The lovastatin butylamide (4.77 g, 10 mmol) was dissolved in toluene (50 ml). Thereafter, benzaldehyde (10.6 g, 10 eq) and p-TsOH (500 mg) were added and stirred during 16 hours at room temperature. A saturated aqueous solution of $NaHCO_3$ was added and the layers were separated. The toluene layer was washed with saturated $NaHCO_3$ (aq), saturated NaCl (aq), dried ($Na_sSO_4$) and evaporated. The residue was purified further by applying column chromatography ($SiO_2$)/n-Hexane/ethyl acetate, which yielded 2.6 g (46%) of the endproduct.

B) Reduction of the Benzylidene Derivative

The benzylidene derivative (2.6 g, 4.6 mmol) was dissolved in toluene (50 ml) and the solution was cooled to 0° C. Then a solution of 1M $LiAlH_4$.2THF (11.5 ml) in toluene was added dropwise while the temperature was kept under 10° C. Then the solution was stirred for 2 hours at 0–5° C. Thereafter 30% NaOH (aq, 1.8 ml) was added and the mixture was stirred for 16 hours at room temperature. The mixture was filtered over Celite, washed with toluene (50 ml) and concentrated to about 50 ml.

C) Formation of Benzylidene Derivative of Simvastatin

Triethylamine (1.9 g, 4.1 eq), dimethylbutyric acid (2.5 g, 4 eq) and dimethylaminopyridine (50 mg) were added to the reaction mixture formed in step 9B and refluxed during 16 hours. The mixture was then poured into water/ethyl acetate and separated. The organic layer was subsequently washed with water, followed by saturated sodium chloride, then dried with sodium sulfate and evaporated, yielding 3.3 g of crude product. Further conversion of the product to simvastatin to be carried out according to the procedure described in Example 5C and 5D, second part.

Example 10
Lovastatin Reduction of the Acetonide of Lovastatin Pyrrolidin Amide:

40 Mg (1.1 mmol) of lithiumaluminiumhydride was added to 0° C. to a solution of 1 g (1.94 mmol) of the acetonide of lovastatin pyrolidin butylamide (prepared analogous to the method described in example 3 by reaction of lovastatin and pyrrolidin) in 20 ml THF. After 18 hours at room temperature the conversion was 50%.

Example 11
Reduction of Lovastatin Butylamide:

To a suspension of $LiAlH_4$ (400 mg 10.5 mmol) in THF (50 ml) was added a solution of lovastatin butylamide (2.25 g, 5 mmol) in THF (25 ml) at 0° C. The mixture was stirred for 16 h at ambient temperature. Moist sodium sulfate ($Na_2SO_4 n2H_2O$, Glauber salt analogue) was added until gas evolution ceased after which dry $Na_2SO_4$ was added. The slurry was filtered over a glass filter and the filtrate was evaporated under reduced pressure to dryness to give a thick brown oil (1.03 g, 53%) HPLC of the crude material; $R_f$=2.93 (and 5.79, starting material).

Example 12
Selective Acylation Reaction on the Nitrogent of the Lovastatin Butylamide Acetonide Alcohol, Thereafter the OH Group can be Acylated:

To a solution of lovastatin butylamamide acetonide alcohol (2.1 g, 5 mmol) and triethylamine (0.8 ml, 5.5 mmol) in toluene (50 ml) was added 1.1 eq. benzoyl chloride (0.64 ml, 5.5 mmol) at 0° C. The reaction mixture was stirred for 16 h at room termperature. A HPLC sample displayed major peaks at $R_f$=6.16 (starting material) and 9.13. After 21 h a peak at 9.67 was coming up. NMR analysis showed a small NH peak and 3 other peaks in the regio 6,5–5 ppm, indicating that the amide is acylated.

Example 13
Reaction of Lovastatin with Ammonia

A suspension of 0.25 g (0.6 mmol) lovastatin in 15 ml of methanol was cooled to 5° C. on an ice/water bath. The methanol was saturated with ammonia (gas) and the mixture was heated for 40 hours at 130° C. in a sealed tube. The reaction mixture contained 43% of the corresponding deacylated product according to HPLC-analysis.

Example 14
Reaction of Lovastatin with n-butylamine

A solution of 0.5 g (1.2 mmol) of lovastatin in 15 ml of n-butylating was heated for 40 hours at 150° C. in a sealed vessel. The reaction mixture contained 12.3% of the corresponding deacylated product according to HPLC analysis. The structure of the deacylated butylamide was confirmed by forming the corresponding acetonide by reaction with p-TsOH and acetone and comparing the acetonide with another sample of acetonide made by the process described in the second part of example 5A.

Example 15
Reaction of Lovastatin with n-heptylamine

A solution of 0.25 g (1.2 mmol) of lovastatin in 10 ml of heptylamine was refluxed for 70 hours. The resulting reaction mixture contained 17% of the corresponding deacylated product according to HPLC analysis.

Example 16
All three deacylated compounds from Examples 13, 14 and 15 were converted into the corresponding acetonide (i.e. by ring closure) by addition of 400 ml of acetone and 5 g of p-TsOH. The mixture was stirred for 1 hour (at room temperature) and then cooled in ice water for 2 hours. The resulting solid was collected by suction and dried.

Example 17
The three acetonide compounds resulting from example 16 were then each individually converted to simvastatin using acylation and ammonium salt conversion reactions as described in steps C and D of Example. 5.

Example 18
Recrystallisation of Simvastatin from Toluene-n-hexane

Crude simvastatin (35 g) was dissolved in toluene (140 ml) while stirring at 60° C. N-hexane (560 ml) was gradually added and the temperature was gradually decreased to 0–5° C. while stirring. After 1 h stirring at the above temperature the precipitated material was collected, washed with a mixture of toluene and n-hexane (1:4 v/v) and dried to give 33 g of the recrystallized product.

Example 19
Recrystallisation of Simvastatin from Methanol-Water

Recrystallized simvastatin (33 g) was dissolved in methanol (300 ml) at room temperature and the solution was treated with activated charcoal. Charcoal was removed by filtration and the product was precipitated by addition of water (450 ml) The suspension was cooled to 5–10° C. and the product was collected, washed with the mixture of methanol and water (1:2 v/v) and dried to yield 31 g of the recrystallized product.

We claim:

1. A process for the formation of highly purified simvastatin from lovastatin, comprising the steps of:
   a) lactone ring opening by reacting lovastatin with an amine to form an amid;
   b) protecting a 1,3-diol moiety with a protecting group;
   c) removing a 2-methylbutyryl group attached by an ester linkage through an oxygen at position 8 of a hexahydronaphthalene ring;
   d) attaching a 2,2-dimethylbutyrate group by forming an ester linkage to a hydroxyl at position 8;
   e) removal of the protecting group;
   f) conversion of the amid to an acid salt; and,
   g) lactone ring closing to form simvastatin.

2. The process of claim 1, wherein the lactone ring opening step is performed by reacting the lactone with at least one compound selected from the group consisting of ammonia, a primary amine, and a secondary amine.

3. The process of claim 1, wherein the lactone ring opening step is performed by reacting the lactone with an amine selected from the group consisting of n-butyl amine, cyclohexylamine, piperidine and pyrrolidine.

4. The process of claim 1, wherein the protecting group is selected from the group which consists of an acetal, a ketal, a cyclic sulfate, a cyclic phosphate and a borate group.

5. The process of claim 1, wherein the simvastatin contains less than about 0.1% simva-oxolactone.

6. The process of claim 1, wherein the simvastatin contains less than about 0.1% anhydrosimvastatin.

7. The process of claim 1, wherein the simvastatin contains less than about 0.1% dihydrosimvastatin.

8. The process of claim 1, wherein the lovastatin is contained in an impure mixture containing as much as about 30% impurities.

9. A process for the formation of a semisynthetic statin of Formula I,

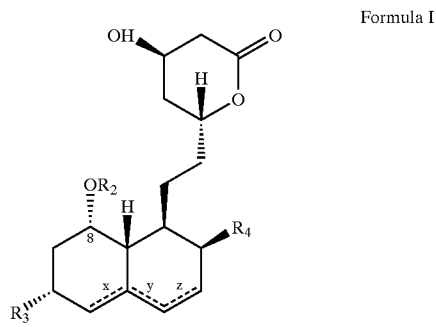

Formula I from a statin of Formula II,

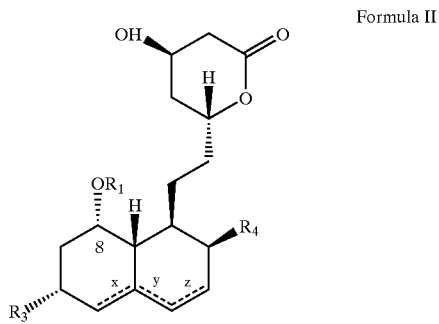

Formula II which comprises the steps of:
a) lactone ring opening by reacting the statin of Formula II with an amine to form an amid;
b) protecting a 1,3-diol moiety with a protecting group;
c) removing a $R_1$ group attached by an ester linkage through an oxygen at position 8 of a hexahydronaphthalene ring;
d) attaching a $R_2$ group by forming an ester linkage to a hydroxyl at position 8;
b) removal of the protecting group;
c) conversion of the amid to an acid salt; and,
g) lactone ring closing to form the semi synthetic statin of Formula I wherein $R_1$ and $R_2$ are both acyl groups linked to the oxygen through an ester bond and $R_3$ and $R_4$ are independently selected from the group consisting of —H, —OH, —$C_{1-10}$ alkyl, —$C_{6-14}$ aryl, and —$C_{6-14}$ aryl-$C_{1-3}$.

10. The process of claim 9, wherein the semisynthetic statin of Formula I contains less than about 0.1% impurities.

11. The process of claim 9, wherein the statin of Formula II is contained in an impure mixture, wherein the mixture includes as much as about 30% impurities.

12. The process of claim 9, wherein the protecting group is selected from the group which consists of an acetal, a ketal, a cyclic sulfate, a cyclic phosphate and a borate group.

13. The process of claim 9, wherein $R_1$ is an acyl group of the form

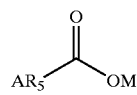

wherein OM is the oxygen which is the hexahydronaphthalene ring substituent at position 8, $R_5$ is selected from the group consisting of —$C_{1-15}$ alkyl, —$C_{3-15}$ cycloalkyl, —$C_{2-15}$ alkenyl, —$C_{2-15}$ alkynyl, -phenyl and -phenyl $C_{1-6}$ alkyl and A is a substituent of $R_5$ selected from the group consisting of hydrogen, a halogen, $C_{1-6}$ alkyl, $C_{1-6}$ alkoxy and $C_{6-14}$ aryl.

14. The process of claim 9, wherein $R_2$ is an acyl group of the form

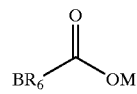

wherein O is the oxygen which is the hexahydronaphthalene ring substituent at position 8, $R_6$ is selected from the group consisting of —$C_{1-15}$ alkyl, —$C_{3-15}$ cycloalkyl, —$C_{2-15}$ alkenyl, —$C_{2-15}$ alkynyl, -phenyl and -phenyl $C_{1-6}$ alkyl and B is a substituent of $R_6$ selected from the group consisting of hydrogen, a halogen, $C_{1-6}$ alkyl, $C_{1-16}$ alkoxy and $C_{6-14}$ aryl.

15. The process of claim 9, wherein the dotted lines at X, Y and Z represent possible double bonds, the double bonds, when any are present, being either X and Z in combination or X, Y or Z alone.

16. The process of claim 9, wherein the lactone ring opening step is performed by reacting the lactone with ammonia, a primary amine, or a secondary amine.

17. The process of claim 9, wherein the lactone ring opening step is performed by reacting the lactone with an amine selected from the group consisting of n-butyl amine, cyclohexylamine, piperidine and pyrrolidine.

* * * * *